(12) United States Patent
Luterotti

(10) Patent No.: US 8,085,157 B2
(45) Date of Patent: Dec. 27, 2011

(54) SMOKE DETECTORS

(75) Inventor: Lorenzo Luterotti, Gorizia (IT)

(73) Assignee: Honeywell International Inc., Morristown, NJ (US)

( * ) Notice: Subject to any disclaimer, the term of this patent is extended or adjusted under 35 U.S.C. 154(b) by 213 days.

(21) Appl. No.: 11/923,313

(22) Filed: Oct. 24, 2007

(65) Prior Publication Data

US 2009/0109043 A1  Apr. 30, 2009

(51) Int. Cl.
*G08B 17/10* (2006.01)
*G08B 21/00* (2006.01)
*G01J 5/02* (2006.01)
*G01N 15/06* (2006.01)
*G01N 21/00* (2006.01)

(52) U.S. Cl. ..... 340/628; 340/630; 340/619; 250/341.8; 250/574; 356/438; 356/437

(58) Field of Classification Search ............ 340/640, 340/630, 578, 511, 693.6, 815.4
See application file for complete search history.

(56) References Cited

U.S. PATENT DOCUMENTS

| 4,742,236 | A | * | 5/1988 | Kawakami et al. | 250/554 |
|---|---|---|---|---|---|
| 5,352,901 | A |   | 10/1994 | Poorman |   |
| 5,880,466 | A | * | 3/1999 | Benner | 250/281 |
| 6,317,511 | B1 | * | 11/2001 | Horiuchi | 382/133 |
| 6,784,990 | B1 | * | 8/2004 | DeFreez et al. | 356/338 |
| 2005/0057365 | A1 | * | 3/2005 | Qualey, III | 340/630 |
| 2005/0173638 | A1 | * | 8/2005 | Powell | 250/341.1 |
| 2007/0064980 | A1 | * | 3/2007 | Knox et al. | 382/128 |
| 2007/0097372 | A1 | * | 5/2007 | Itagaki | 356/437 |
| 2007/0171396 | A1 | * | 7/2007 | Harris et al. | 356/28 |
| 2008/0204718 | A1 | * | 8/2008 | Trainer | 356/73 |

FOREIGN PATENT DOCUMENTS

| GB | 2 259 763 A | 3/1993 |
|---|---|---|
| GB | 2 273 769 A | 6/1994 |
| GB | 2 330 410 A | 4/1999 |
| WO | WO 2006/049613 A1 | 5/2006 |

OTHER PUBLICATIONS

Robin A. Aspey, Karl J. Brazier, Joe W. Spencer, Multiwavelength Sensing of Smoke Using a Polychromatic LED: Mie Extinction Characterization Using HLS Analysis, IEEE Sensors Journal, 2005, pp. 1-7.

Darryl W. Weinert, Thomas G. Cleary, George W. Mulholland, Paula F. Beever, Light Scattering Characteristics and Size Distribution of Smoke and Nuisance Aerosols, Jun. 2003, pp. 209-220, Fire Safety Science—Proceedings of the Seventh International Symposium.

Extended European Search Report, dated Feb. 2, 2009 corresponding to European application No. 08167321.2.

* cited by examiner

*Primary Examiner* — Daniel Wu
*Assistant Examiner* — Pameshanand Mahase
(74) *Attorney, Agent, or Firm* — Husch Blackwell LLP

(57) ABSTRACT

A multi-frequency photoelectric smoke detector includes a multi-frequency, source and an multi-frequency sensing array. The array can be part of a solid state camera which can be used to sense scattered multi-frequency light. Multiple wavelength signals, red, blue green for example, emitted by the camera can be analyzed to determine a degree of airborne particulate matter in a sensing region between the source and the array.

18 Claims, 2 Drawing Sheets

SMOKE DETECTORS

FIELD

The invention pertains to photoelectric smoke detectors. More particularly, the invention pertains to such detectors which incorporate a multi-frequency light source and a light sensor to perform multiple angle, multiple wavelength scattering analysis.

BACKGROUND

Current photoelectric smoke detection technologies and products are several decades old. The basic principle includes the use of a light emitter (nowadays usually IR led) and a light sensitive receiver (usually PIN photodiode) placed out of sight each other.

The emitter is energized, or pulsed, periodically. When smoke is present the receiver detects the increasing scattered light signal. A photocurrent to voltage circuit (transimpedance amplifier) is usually used to measure smoke presence and eventually determine alarm condition.

The main strengths of this technology are low cost simplicity, fairly broad applicability and low power consumption. The weakness of the approach are poor nuisance immunity (dust, steam, etc., might set the detector in alarm), difficult to detect very small and/or dark absorbing particles such as those coming from some flaming fires (which usually requires Ion detectors). An optical detector covering the product range usually covered by ion detectors would be a benefit under the production, storage, installation, maintenance and end of life management perspective.

There thus is a need for approaches to photoelectric smoke detection which take advantage of currently available components. Preferably, using such components, more sensitive, nuisance immune, detectors could be produced. It would also be desirable if costs were comparable to those of existing photoelectric detectors.

DETAILED DESCRIPTION

Figure 1:
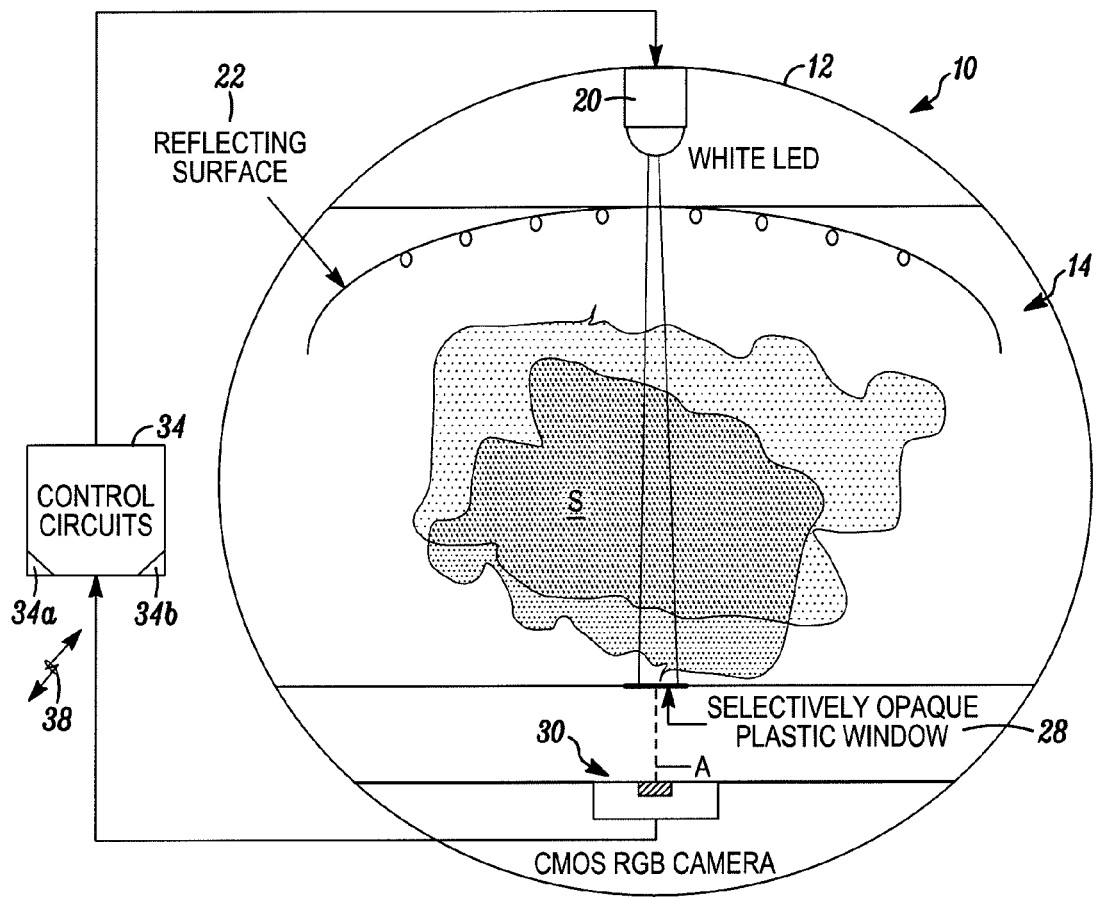
FIG. 1 is a block diagram of a first embodiment of the invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

Embodiments of the invention provide a more complete and powerful quantitative and qualitative analysis of suspended particles. As a result, more sensitive detection and improved nuisance immunity should be achievable, Using a broad band light source such as a white LED and preferably getting benefit of RGB data available from a low cost low resolution (VGA or lower) color CMOS camera extinction, front scattering (very small angles) and back scattering analysis of received signals over three different wavelengths spectrum can be achieved. Such information can be used in multi-frequency detection processing resulting in very early and robust—in terms of nuisance immunity—fire detection.

While there are several different embodiments of this invention one of the preferred provides an in-sight arrangement with a white led emitter and a multi-frequency sensor, such as those found in CMOS color cameras, functioning as a receiver. Between the emitters and receivers there are a few centimeters (approx 5 cm) called the detection volume—where smoke can enter.

The emitters can exhibit a very narrow (<5°) beam by including a selected lens with or without mechanical flanges. Close to and in front of the sensor there is a partially opaque plastic member (like a vertical pillar), or an optical filter. When no smoke is present the beam hits the transparent pillar and the sensor (a low CMOS camera in the preferred embodiment) detects a dark picture with a small white dot in the center.

Several configurations (absorber/thickness change) might be used to avoid camera saturation due to a high intensity level of central white dot. When small particles such as smoke, dust or mist enter the detection volume, scattering of the emitted beam takes place. The camera can see the white dot becoming larger and larger and with smooth—blue colored—edges. The scattering phenomena is highly wavelength dependent: hence, blue rays exhibit a different scattering intensity than, for example red or green rays. Moreover the back scattering analysis might be implemented the same detector by locating a selected reflecting surfaces close to emitter.

The sensor will thereby detect the spectral response (RGB/HUE analysis) of several physical light-particle interaction phenomena: front scattering over a wide range of angles (5-45°), back scattering and absorption/extinction (reduction of light intensity of central spot). Polarization/scattering ellipsometry analysis could also be implemented by the analysis method.

A final benefit of the approach would be achieving ultra-sensitive small particle detection: scattering at extremely narrow angles is at least a 2 orders of magnitude higher compared to current photoelectric smoke detectors arrangement (typical detection angle is approximately 45°). Moreover as the wavelength to particle diameter ratio dominates the scattering physic, blue light scattering from sub micron particles, such as those released from oxygen rich, free burning flames is much higher then scattering from IR radiation. Preferably, high nuisance immunity could be achieved through selected signal processing of all those different types of scattering phenomena.

Another possible embodiment may provide an additional light guide for ambient light supervision. Such an input could be used for day/night sensitivity settings as well as flame detection in a multiple criteria algorithm. Electrowetting lenses already commercially available in various consumer products for example, mobile phones, can be used to adjust camera, or sensor, focus length to detect forward, or, back scattering as desirable.

FIG. 1 illustrates a block diagram of a detector 10 which embodies the present invention. Detector 10 includes a housing 12 which defines an internal sensing region 14. The housing 12 includes at least one inflow port and at least one outflow port into the region 14 for air borne particulate matter indicated generally at S. The air borne particulate matter S could be indicative of smoke in a larger region adjacent to the detector 10.

Detector 10 also includes a multi-frequency source of radiant energy 20. The source 20 could be implemented with a light emitting diode, LED, which emits white light along an axis A. Light from the source 20 is emitted as a heat radiating energy R into the region 14 and is scattered by air borne particulate matter S present therein.

As discussed in more detail, subsequently, housing 10 can also carry optional reflecting surfaces 22. A selectively opaque optical window 28, which could be in the form of a parallelepiped, or, cylindrical plastic member is located on the central axis A of the radiant energy beam R relative to the source 20. Alternately, an optical filter can be interposed between the source and a sensor as discussed below.

A multi-frequency sensor 30, which could be implemented as a CMOS RGB camera element is carried by housing 10 on the axis A of the radiant energy beam R displaced from the window 28. The window, or filter, 28 is located between the source 20 and sensor element 30. Sensor 30 could be implemented as a multi-dimensional array or matrix.

Control circuits 34 can be coupled to the source 20 for purposes of pulsing and intermittingly energizing same such that source 20 produces the radiant energy beam R. Control circuits 34 can be coupled to the sensor 30 and receive multi-frequency outputs there from. In a preferred embodiment, the multi-frequency outputs correspond to the red, green and blue frequencies.

A detector 10 and sensor 30 can generate signals for control circuits 34 enabling the circuits 34 to carry out absorption/forward scattering/backward scattering analysis of the received radiant energy beam R. The analysis indicates a level of particulate matter S in the region 14. Detectors, such as detector 10, are advantageously potentially highly sensitive, by taking advantage of narrow angle front scattering, and have high noise immunity.

Reflecting surfaces 24 make it possible for the sensor 30 to receive back scattered radiant energy which can be analyzed.

Figure 2:
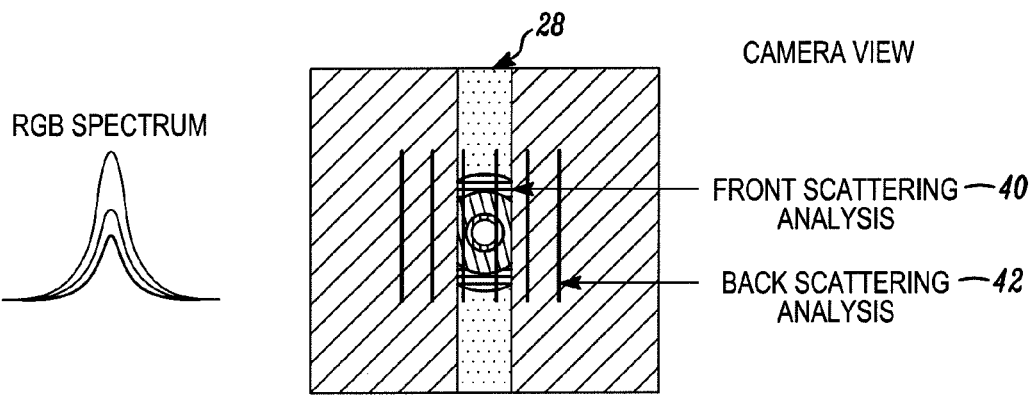
FIG. 2 illustrates multi-scattering effects associated with the embodiment of FIG. 1.

FIG. 2 illustrates representative radiant energy components incident on the array 30. Array 30 generates signals indicative of the components of radiant energy impinging thereon. The opaque window 28 limits incident radiant energy falling directly onto the sensor 30 to avoid saturation thereof.

Forward scattering analysis 40 can be carried out in response to incident blue frequency components and respective edges incident on array 30. Back scattering analysis 42, of radiant energy from the reflective surfaces 22 incident on array 30 can be carried out at circuits 34.

Those of skill in the art will understand that exemplary control circuits 34 could be implemented with a programmable processor 34a and associated executable software 34b. Control circuits 34 could be in communication with an environmental monitoring system, not shown, via a wired or wireless medium 38. Those of skill in the art will also understand that the control circuits 34 can carry out a variety of analysis methods for purposes of analyzing signals received from array 30.

Figure 3:
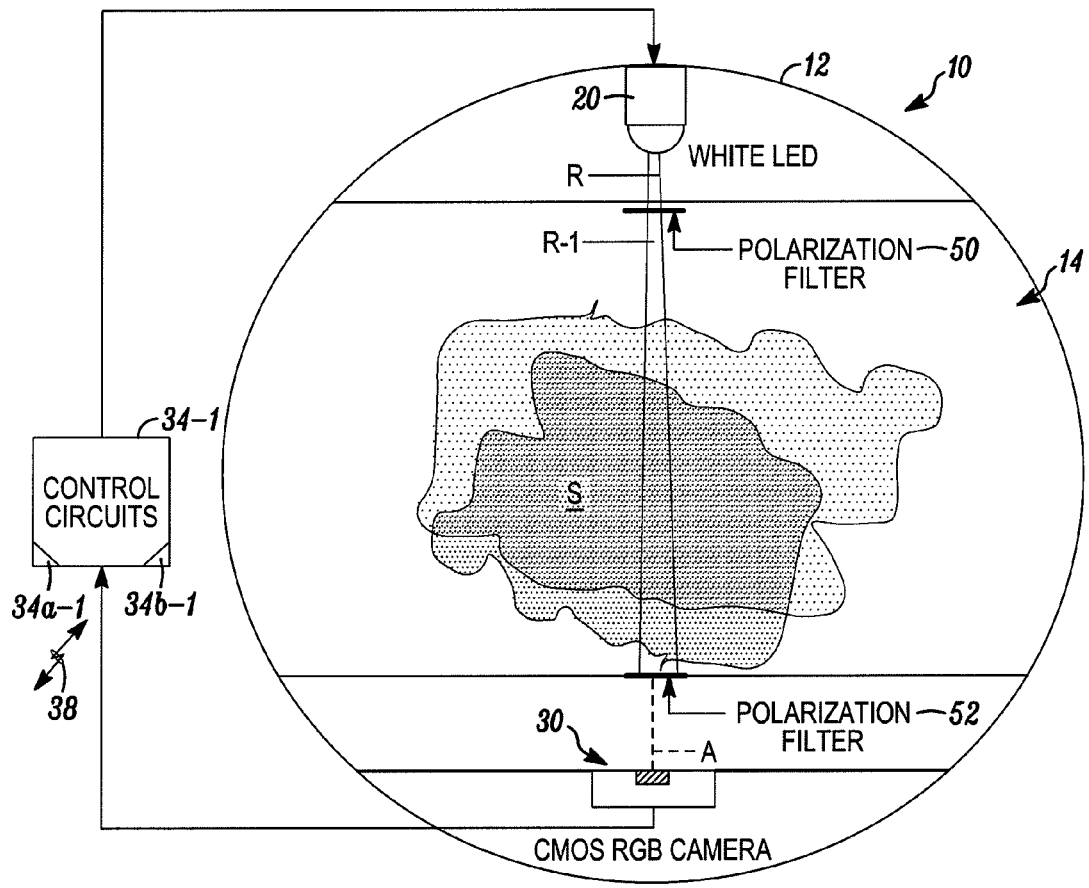
FIG. 3 is a block diagram of a second embodiment of the invention.

FIG. 3 illustrates an alternate embodiment, smoke detector 10-1. Structures associated with Identification numerals in FIG. 3 which are identical to those of FIG. 1 were previously discussed and no further discussion thereof is needed.

Unlike the detector 10, detector 10-1 includes a polarization filter 50, such as an octagonal polarizing filter located on the axis A of the radiant energy beam R emitted from the source 20. The polarized beam R-1 which traverses region 14 has been emitted from polarizing filter 50.

A second polarizing filter 52 adjacent to the sensor or camera 30 could be implemented as a double orthogonal polarizing filter. Filter 52 as a vertical plane polarizing section 52a and a horizontal plane polarizing section 52b.

The filter 52 is located generally displaced from sensor 30 in the same vicinity as the opaque plastic window 28 of the detector 10.

Figure 4:
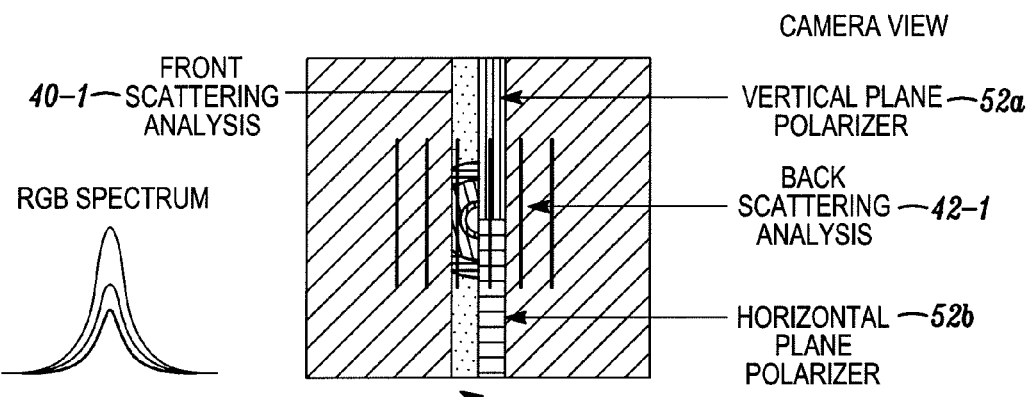
FIG. 4 illustrates multi-scattering effects associated with the embodiment of FIG. 3.

FIG. 4 illustrates various types of signals receivable off of the array or camera 30 generated by incoming incident beam R-1 subsequent to having passed through polarization filter 52. Forward scattering data can be analyzed 40-1 off of signals from radiant energy incident on the array 30. Where reflectors such as reflectors 22 might be present, back scattered radiant energy incident on array 30 could be analyzed 42-1.

As those of skill in the art will understand analysis can be carried out at control circuits 34-1 via processor 34a-1 and associated executable software 34b-1. Alternately, data representative of the multi-frequency signals received from sensor 30 could be transmitted via wired or wireless medium 38 to a displaced regional monitoring unit. Those of skill in the art will also understand details of analysis are not limitations of the present invention.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A smoke detector comprising:
   a hollow housing, the housing having at least one ambient inflow port and at least one ambient atmosphere outflow port;
   a single source of multi-frequency radiant energy carried in the housing, the source emits a beam of multi-frequency white-light energy along a first axis across and within the housing;
   a multi-frequency responsive sensor matrix positioned in the housing on the first axis, the matrix emitting a plurality of frequency responsive electrical signals in response to sensed incident radiant energy from the source and in response to front scattered and to reflected back scattered radiant energy;
   at least one of an optical filter, or, barrier positioned on the axis between the source and the matrix, the beam hits the optical filter or barrier and in the absence of particulate the multi-frequency responsive sensor matrix detects a dark picture with a white dot in the center and in the presence of particulate a progressively larger white dot; and
   a reflector carried in the housing between the single source and the optical filter or barrier to reflect back scattered radiant energy to the sensor matrix, wherein particulate matter in the housing scatters a portion of the beam of energy from the single source to create the back scattered energy, the sensor matrix thereby detects the spectral response of several physical light-particle interaction phenomenon including front scattering over a predetermined range of angles, backscattering and absorption or extinction reducing a light intensity of the central spot.

2. A detector as in claim 1 where the optical barrier is selectively transmissive of the beam; the single source is a white-light LED and the matrix is a CMOS RGB camera.

3. A detector as in claim 2 where the plurality of electrical signals is responsive to air borne particulate matter in the ambient atmosphere in the housing.

4. A detector as in claim 2 where the electrical signals each exhibit a respective amplitude, the amplitude being indicative of air borne particulate matter in the housing.

5. A detector as in claim 4 with the respective amplitudes reflective of a degree of scattering of the beam in response to the air borne particulate matter in the housing.

6. A detector as in claim 1 wherein different scattered frequency components of the beam are indicative of air borne particulate matter in the housing.

7. A detector as in claim 6 which includes a control unit, coupled to the electrical signals emitted by the array, the control unit, responsive to received electrical signals, establishes a degree of air borne particulate matter in the housing.

8. A detector as in claim 7 where the control unit has an output port and emits therefrom at least one indication of the degree of air borne particulate matter in the housing.

9. A detector as in claim 8 where the optical bather, at least in part, limits radiant energy incident on the array in the absence of a predetermined degree of air borne particulate matter in the housing.

10. A detector as in claim 9 to which includes a polarizing filter, adjacent to the source, on the first axis, a polarized beam is transmitted across the housing.

11. A detector as in claim 10 which includes a selected octagonal polarizing filter located adjacent to the sensor, on the first axis between the emitted polarized beam and the sensor array.

12. A method of detecting air born particulate matter in a region comprising:
   generating a multi-frequency single beam of radiant white-light energy;
   projecting the beam across a predetermined region to a sensor along an axis;
   blocking the beam, to a predetermined degree, in the absence of air borne particulate matter in the region within at least one of an optical filter or barrier, the beam hitting the optical filter or barrier and the sensor detects a dark picture with a white dot in the center;
   scattering a portion the beam in response to air borne particulate matter in the region to create back scattered radiant energy, the white dot becomes relatively larger;
   sensing received frequency components of the beam scattered in the region in response to reflecting, with a reflector carried within the housing, the back scattered radiant energy toward a location where received frequency components are sensed, the reflector is located between a location where the multi-frequency single beam of radiant white-light energy is generated and the location where received frequency components are sensed, wherein the location where received frequency components are sensed is on the axis; and
   sensing both incident radiant energy and the back scattered radiant energy reflected by the reflector to the location of the sensor where received frequency components are sensed, the sensor thereby detects the spectral response of several physical light-particle interaction phenomenon including front scattering over a predetermined range of angles, backscattering and absorption or extinction reducing a light intensity of the central spot.

13. A method as in claim 12 where the radiant energy is a white-light LED energy and sensing includes sensing reflected radiant energy via a CMOS RGB camera.

14. A method as in claim 13 which includes evaluating, on a per-frequency basis at least one of, a degree of sensed, back scattered radiant energy, or, a degree of sensed forward scattered radiant energy.

15. A method as in claim 14 which includes generating at least one output signed indicative of the evaluating.

16. A method as in claim 15 where evaluating includes establishing the absence of a predetermined degree of sir borne particulate matter in the housing.

17. A method as in claim 13 where generating includes generating a polarized multi-frequency beam of radiant energy.

18. A method as in claim 17 which includes, prior to sensing, polarizing the received frequency components.

* * * * *